United States Patent
Bogdanovic et al.

(10) Patent No.: US 6,211,414 B1
(45) Date of Patent: Apr. 3, 2001

(54) PROCESS FOR PREPARING ALDEHYDES BY HYDROFORMYLATION

(75) Inventors: Sandra Bogdanovic, Frankfurt am Main; Helmut Bahrmann, Hamminkeln; Carl-Dieter Frohning, Wesel; Ernst Wiebus, Oberhausen, all of (DE)

(73) Assignee: Celanese GmbH (DE)

( * ) Notice: Subject to any disclaimer, the term of this patent is extended or adjusted under 35 U.S.C. 154(b) by 0 days.

(21) Appl. No.: 09/341,835

(22) PCT Filed: Dec. 30, 1997

(86) PCT No.: PCT/EP97/07315
§ 371 Date: Aug. 31, 1999
§ 102(e) Date: Aug. 31, 1999

(87) PCT Pub. No.: WO98/30527
PCT Pub. Date: Jul. 16, 1998

(30) Foreign Application Priority Data

Jan. 13, 1997 (DE) ............................................... 197 00 805

(51) Int. Cl.$^7$ .................................................. C07C 45/50
(52) U.S. Cl. ........................................... 568/454; 568/451
(58) Field of Search ..................... 568/451, 454; 502/24

(56) References Cited

U.S. PATENT DOCUMENTS

| 3,404,188 | 10/1968 | Privette et al. ....................... 260/617 |
| 4,399,312 | * 8/1983 | Russell et al. ....................... 568/454 |
| 5,091,350 | * 2/1992 | Cornils et al. ......................... 502/24 |

FOREIGN PATENT DOCUMENTS

| 0157316 | 10/1985 | (EP) . |
| 2314910 | 1/1977 | (FR) . |
| 2489308 | 3/1982 | (FR) . |

* cited by examiner

*Primary Examiner*—Sreeni Padmanabhan
(74) *Attorney, Agent, or Firm*—Bierman, Muserlian and Lucas

(57) ABSTRACT

The invention concerns a process for preparing aldehydes by reacting with hydrogen and carbon monoxide at a temperature of between 20 and 170° C. and a pressure of between 1 and 300 bar an olefinically unsaturated $C_3$–$C_5$ compound in the presence of an aqueous phase containing rhodium and sulphonated triarylphosphines as catalyst and between 1 and 35 wt % of a compound of formula (1), $R(OCH_2CH_2)_nOR^1$, R standing for hydrogen, a straight-chain or branched $C_1$–$C_4$ alkyl group or a $C_1$–$C_4$ hydroxyalkyl group, $R^1$ standing for hydrogen or a methyl group, and n standing for an integer from 3 to 50.

37 Claims, No Drawings

PROCESS FOR PREPARING ALDEHYDES BY HYDROFORMYLATION

This application is a 371 of PCT/EP97/07315 filed Dec. 30, 1997.

The present invention relates to a process for preparing aldehydes by reacting olefinic compounds having from 3 to 5 carbon atoms with hydrogen and carbon monoxide at superatmospheric pressure in the presence of an aqueous phase comprising rhodium and sulfonated triarylphosphines as catalyst.

It is known that aldehydes and alcohols can be prepared by reacting olefins with carbon monoxide and hydrogen. The reaction is catalyzed by hydrido-metal carbonyls, preferably those of metals of group VIII of the Periodic Table. Besides cobalt, which is widely used industrially as catalyst metal, rhodium has recently achieved increasing importance. In contrast to cobalt, rhodium allows the reaction to be carried out at low pressure; in addition, straight-chain n-aldehydes are preferentially formed and iso-aldehydes are formed to only a subordinate extent. Finally, significantly less hydrogenation of the olefins to saturated hydrocarbons occurs when using rhodium catalysts than when using cobalt catalysts.

In the processes which have been introduced in industry, the rhodium catalyst is used in the form of modified hydrido-rhodium carbonyls which contain additional ligands which may, if appropriate, be used in excess. Tertiary phosphines or phosphites have been found to be particularly useful as ligands. Their use makes it possible to reduce the reaction pressure to below 30 MPa.

However, the separation of the reaction products and the recovery of the catalysts homogeneously dissolved in the reaction product create problems in this process. In general, the reaction product is distilled from the reaction mixture. In practice however, owing to the thermal sensitivity of the aldehydes and alcohols formed, this method can only be employed in the hydroformylation of lower olefins, i.e. olefins having up to about 5 carbon atoms in the molecule.

The hydroformylation of long-chain olefins or olefinic compounds containing functional groups forms products having a high boiling point and these cannot be separated from the homogeneously dissolved rhodium complex catalyst by distillation. The thermal stressing of the material being distilled leads to considerable losses of desired products due to thick oil formation and of catalyst due to decomposition of the rhodium complexes.

The separation of the catalyst by thermal means is avoided by use of water-soluble catalyst systems. Such catalysts are described, for example, in DE-C 26 27 354. The solubility of the rhodium complexes is here achieved by use of sulfonated triarylphosphines as constituent of the complex. In this process variant, the catalyst is separated from the reaction product after the hydroformylation reaction is complete simply by separating the aqueous and organic phases, i.e. without distillation and thus without additional thermal process steps. A further feature of this procedure is that n-aldehydes are formed with high selectivity from terminal olefins and iso-aldehydes are formed to only a very subordinate extent. Apart from sulfonated triarylphosphines, carboxylated triarylphosphines are also used as constituents of water-soluble rhodium complexes.

The use of water-soluble catalysts has been found to be useful in the hydroformylation of lower olefins, in particular propene and butene. However, if higher olefins such as pentene or hexene are used, the reaction rate is noticeably reduced. An industrial-scale reaction is frequently no longer as economical as desired when using olefins having four or more carbon atoms.

In order to increase the conversion and/or the selectivity of the reaction to n-aldehydes in the hydroformylation of higher olefins by means of water-soluble catalysts, the addition of an amphiphilic reagent (DE 31 35 127 A1) or a solubilizer (DE 34 12 335 A1) has been recommended.

According to both DE 31 35 127 A1 and DE 34 12 335, very high conversions are obtained using quaternary ammonium salts which have a long-chain alkyl radical, while nonionic substances based on polyethylene glycol lead to comparatively low conversions.

As can be seen from Table 7 in DE 31 35 127, the hydroformylation of 1-dodecene by means of rhodium and monosulfonated triphenylphosphine (3-$Ph_2PC_6H_4SO_3Na$) without addition of an amphiphilic reagent leads to a conversion of 56% (Example 77), while the addition of $C_{12}H_{25}(OCH_2CH_2)_{23}OH$ (="Brij 35") leads to a reduction in the conversion to 37% (Example 78).

According to DE 34 12 335 (Table 4), the hydroformylation of hexene by means of rhodium and trisodium tri(m-sulfophenyl)phosphine without addition of a solubilizer leads to a conversion of 36% (Example 10), while addition of 2.5% of triethylene glycol (Example 14) or 5% of polyglycol 200 (Example 11) gives a conversion of 43.5% or 43% respectively. The addition of the solubilizer results in no significant increase in the conversion, and increasing the amount of solubilizer from 2.5% to 5% also does not increase the conversion. On the other hand, a very high conversion, namely 86%, is achieved with an addition of 2.5% of trimethylhexadecylammonium bromide.

However, the use of quaternary ammonium salts as amphiphilic reagent or solubilizer is not without problems because of the poor biodegradability of these compounds. Thus, the presence of quaternary ammonium salts in wastewater leads to difficulties in wastewater treatment.

Amphiphilic reagents and solubilizers serve to aid mass transfer between the individual phases and thus the miscibility of aqueous catalyst phase and organic phase. An increase in the miscibility of aqueous catalyst phase and organic phase means an increased solubility of the organic phase in the aqueous phase and of the aqueous phase in the organic phase. In this way, increasing amounts of amphiphilic reagent and solubilizer and also rhodium and water-soluble phosphine can get into the organic phase and be carried off with the organic phase after phase separation.

Furthermore, it is to be expected that with increasing miscibility of aqueous catalyst phase and organic phase the demixing required for phase separation will no longer take place to a sufficient extent, if at all, as a result of the formation of emulsions or solutions. A corresponding increase in the miscibility is to be expected particularly when the amount of amphiphilic reagents and solubilizers added is increased.

Increased discharge of rhodium, water-soluble phosphine and amphiphilic reagent or solubilizer via the organic phase is, like reduced demiscibility of the phases, undesirable, since the rhodium, water-soluble phosphine and amphiphilic reagent or solubilizer should remain in the aqueous catalyst phase and good demiscibility is an essential prerequisite for the separation of organic and aqueous phases which is necessary at the end of the hydroformylation.

In view of the above considerations, there is a need for a process which avoids the abovementioned disadvantages and, in addition, can be implemented industrially in a simple manner.

This object is achieved by a process for preparing aldehydes. It comprises reacting an olefinically unsaturated compound having from 3 to 5 carbon atoms with hydrogen and carbon monoxide at from 20 to 170° C. and from 1 to 300 bar in the presence of an aqueous phase comprising rhodium and sulfonated triarylphosphines as catalyst and from 1 to 35% by weight of a compound of the formula (1) $R(OCH_2CH_2)_nOR^1$, where, in the formula (1), R is hydrogen, a straight-chain or branched alkyl radical having from 1 to 4 carbon atoms or a hydroxyalkyl radical having from 1 to 4 carbon atoms, $R^1$ is hydrogen or a methyl radical, in particular hydrogen, and n is an integer from 3 to 50.

In view of the abovementioned findings of DE 34 12 335 (Table 4, Examples 10, 14 and 11) and DE 31 35 127 (Table 7, Examples 77 and 78) for the hyroformylation of hexene and dodecene, it was not to be expected that addition of compounds of the formula (1) $R(OCH_2CH_2)_nOR^1$ in the abovementioned amounts in the reaction of olefinic compounds having only 3 to 5 carbon atoms would lead to a significant increase in the conversion and at the same time to a high selectivity in respect of the formation of n-aldehydes.

If propene is hydroformylated in the presence of an aqueous phase comprising rhodium and trisulfonated triphenylphosphine, a very high reaction rate is obtained in the absence of an amphiphilic reagent or solubilizer.

In view of this, it is surprising that a comparatively small addition of compounds of the formula (1) leads to a noticeable increase in the already very high propylene conversion rate. Furthermore, it was not to be expected that despite this conversion increase the ratio of formation of n-butanal to iso-butanal would be influenced only very slightly. The formation of n-butanal is reduced by only a very small amount compared to the procedure without addition of compounds of the formua (1).

In view of the great influence which even a comparatively small addition of compounds of the formula (1) has on the propylene conversion, it is also unexpected that rhodium, the sulfonated triarylphosphine and the compound of the formula (1) remain virtually completely in the aqueous phase and do not get into the organic phase and are not lost from the aqueous phase via the organic phase.

It is also generally surprising that in the hydroformylation of olefinic compounds having from 3 to 5 carbon atoms, even the addition of comparatively large amounts of compounds of the formula (1) $R(OCH_2CH_2)_nOR^1$ does not cause a significant increase in the amount of rhodium and sulfonated triarylphosphine in the organic phase and thus to increased discharge of the catalyst via the organic phase.

In addition, it was not to be expected that, despite the comparatively large amounts of compounds of the formula (1), the demiscibility of organic phase and aqueous catalyst phase is high enough to ensure the separation of organic phase and aqueous catalyst phase. Surprisingly, difficult-to-separate emulsions or homogeneous phases or solutions which cannot be separated are not formed.

The aqueous phase comprising the catalyst and the compound of the formula (1) $R(OCH_2CH_2)_nOR^1$ can be prepared in a comparatively simple way by dissolving a water-soluble rhodium salt, the sulfonated triarylphosphines and the compound of the formula (1) in water. Suitable rhodium salts are, without making any claim to completeness: rhodium(III) sulfate, rhodium(III) nitrate, rhodium(III) carboxylates such as rhodium acetate, rhodium propionate, rhodium butyrate and rhodium 2-ethylhexanoate.

The aqueous phase can be used directly in the hydroformylation or subjected beforehand to a preformation of the catalyst under reaction conditions and used subsequently in preformed form.

The olefinic compound used can be an aliphatic olefin or cycloaliphatic olefin having from 3 to 5 carbon atoms, in particular an aliphatic olefin having from 3 to 5 carbon atoms, preferably an aliphatic α-olefin having from 3 to 5 carbon atoms.

The olefinic compound can contain one or more carbon-carbon double bonds. The carbon-carbon double bond can be in a terminal or internal position. Preference is given to olefinic compounds having a terminal carbon-carbon double bond.

Examples of α-olefinic compounds (with a terminal carbon-carbon double bond) are alkenes, alkyl alkenoates, alkenyl alkanoates, alkenyl alkyl ethers and alkenols.

Without claiming completeness, olefinic compounds which may be mentioned are propene, cyclopropene, butene, pentene, butadiene, pentadiene, cyclopentene, cyclopentadiene, allyl acetate, vinyl formate, vinyl acetate, vinyl propionate, allyl methyl ether, vinyl methyl ether, vinyl ethyl ether, and allyl alcohol, in particular propene, 1-butene, industrially available mixtures containing essentially 1-butene and 2-butene, and 1-pentene.

For the purposes of the present invention, sulfonated triarylphosphines are phosphines which contain one or two phosphorus atoms, which have three aryl radicals per phosphorus atom, where the aryl radicals are identical or different and are each a phenyl, naphthyl, biphenyl, phenylnaphthyl or binaphthyl radical, in particular a phenyl, biphenyl or binaphthyl radical, and the aryl radicals are connected to the phosphorus atom either directly or via a —$(CH_2)_x$— group, where x is an integer from 1 to 4, in particular from 1 to 2, preferably 1, and which contain at least three —$(SO_3)M$ groups, where M are identical or different and are each H, an alkali metal ion, an ammonium ion, a quaternary ammonium ion, a ½ alkaline earth metal ion or ½ zinc ion, in particular an alkali metal ion, an ammonium ion or a quaternary ammonium ion, preferably an alkali metal ion. The —$SO_3M$ groups are usually located as substituents on the aryl radicals and give the triarylphosphines the required water solubility.

As sulfonated triarylphosphines containing one phosphorus atom, preference is given to using compounds of the formula (2)

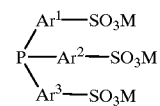

where $Ar^1$, $Ar^2$ and $Ar^3$ are identical or different and are each a phenyl or naphthyl radical, in particular a phenyl radical, and M are identical or different, in particular identical, and are each an alkali metal ion, an ammonium ion, a quaternary ammonium ion or a ½ alkaline earth metal ion or ½ zinc ion, in particular an alkali metal ion or ammonium ion, preferably an alkali metal ion, particularly preferably a sodium ion.

Trisodium tri(m-sulfophenyl)phosphine is particularly suitable as sulfonated triarylphosphine. This trisodium salt of tri(meta-sulfophenyl)phosphine contains, owing to its preparation by sulfonation of triphenylphosphine, amounts of monosulfonated and disulfonated compounds.

Trisodium tri(m-sulfophenyl)phosphine corresponds to the following formula:

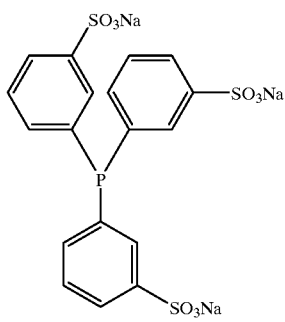

The sulfonated triarylphosphines containing two phosphorus atoms can, for example, contain a radical —$(CH_2)_x$—Ar—Ar—$(CH_2)_x$—, where x is an integer from 1 to 4, in particular from 1 to 2, preferably 1, Ar—Ar is biphenyl or binaphthyl, the —$(CH_2)_x$— group is, via one bond, in each case located in the ortho position to the aryl-aryl bond Ar—Ar connecting the two aryl radicals and is connected via the other bond to a phosphorus atom which in each case bears two further, identical or different aryl radicals, in particular phenyl radicals. These triarylphosphines containing two phosphorus atoms have at least three —$SO_3M$ groups, in particular from 4 to 8 —$SO_3M$ groups, where M is as defined above. The —$SO_3M$ groups are usually located on the aryl radicals of the radical —$(CH_2)_x$—Ar—Ar—$(CH_2)_x$— and on the two further aryl radicals which are connected to the phosphorus.

Examples of such sulfonated triarylphosphines containing two phosphorus atoms are, without making any claim as to completeness, represented by the formulae (3) and (4) below:

(3)

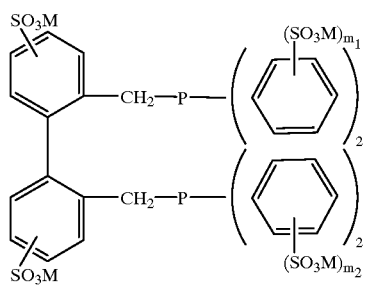

In (3), $m_1$ and $m_2$ are each, independently of one another, 0 or 1, with the compound of the formula (3) containing from three to six —$SO_3M$ groups.

(4)

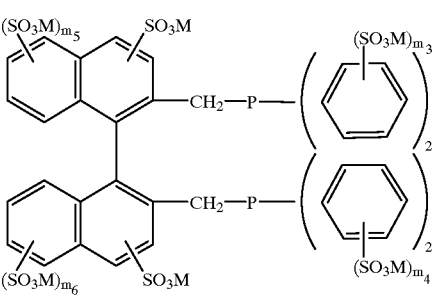

In (4), $m_3$, $m_4$, $m_5$ and $m_6$ are each, independently of one another, 0 or 1, with the compound of the formula (4) containing from four to eight, in particular from five to six, —$SO_3M$ groups.

Since the compounds (3) and (4) are prepared by sulfonation of the corresponding phosphines of the formulae (3a) and (4a) which contain no —$SO_3M$ groups, (3a)

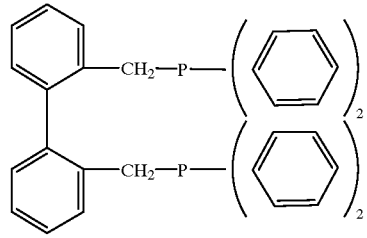

(4a)

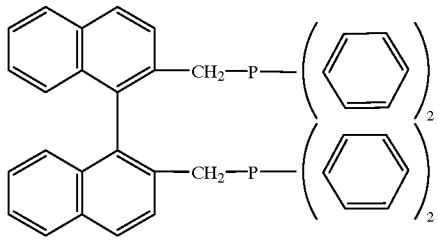

they are usually obtained in the form of mixtures of compounds containing different numbers of —$SO_3M$ groups. Thus, a compound of the formula (3) or (4) which contains, for example, three —$SO_3M$ groups also contains compounds having only two —$SO_3M$ groups as well as compounds having four or five —$SO_3M$ groups. A compound of the formula (3) or (4) having, for example, five —$SO_3M$ groups usually also contains compounds having only three or four —$SO_3M$ groups as well as compounds having six or seven —$SO_3M$ groups.

Compounds of the formula (3) have a maximum of six —$SO_3M$ groups, while compounds of the formula (4) have a maximum of eight —$SO_3M$ groups.

For this reason, mixtures of compounds of the formula (3) or (4) having a different number of —$SO_3M$ groups are generally used.

The above-described sulfonated triarylphosphines have, owing to their sulfonate radicals, a solubility in water which is sufficient for carrying out the process.

The aqueous phase comprising rhodium and the compounds of the formula (2) as catalyst and the compound of the formula (1) is usually used in an amount corresponding to from $2\times10^{-6}$ to $5\times10^{-2}$ mol, in particular from $5\times10^{-5}$ to $5\times10^{-2}$ mol, preferably from $1\times10^{-4}$ to $1\times10^{-3}$ mol, of rhodium per mol of olefinic compound.

The amount of rhodium also depends on the type of olefinic compound to be hydroformylated. Although lower catalyst concentrations are possible, in some cases they can prove to be not particulary appropriate, since the reaction rate can be too low and therefore not economical enough. The catalyst concentration can be up to $1\times10^{-1}$ mol of rhodium per mol of olefinic compound, but comparatively high rhodium concentrations give no particular advantages.

The aqueous phase comprising rhodium and sulfonated triarylphosphines as catalyst and the compound of the formula (1) $R(OCH_2CH_2)_nOR^1$ is usually used in a volume ratio to the olefinic compound of from 10:1 to 1:10, in particular from 5:1 to 1:5, preferably from 2:1 to 1:2.

Rhodium and sulfonated triarylphosphines are used in a molar ratio of from 1:5 to 1:2000.

If use is made of a sulfonated triarylphosphine containing one phosphorus atom, for example a compound of the formula (2), rhodium and sulfonated triarylphosphine are usually used in a molar ratio of from 1:10 to 1:1000, in particular from 1:50 to 1:200, preferably from 1:80 to 1:120.

If use is made of a sulfonated triarylphosphine containing two phosphorus atoms (for example a compound of the formula (3) or (4)), rhodium and sulfonated triarylphosphine are usually used in a molar ratio of from 1:5 to 1:100, in particular from 1:5 to 1:50, preferably from 1:8 to 1:15.

The aqueous phase contains from 20 to 2000 ppm of rhodium. If a sulfonated triarylphosphine containing one phosphorus atom, for example a compound of the formula (2), is employed, use is in most cases made of an aqueous phase containing from 100 to 1000 ppm, in particular from 200 to 500 ppm, preferably from 300 to 400 ppm, of rhodium.

If a sulfonated triarylphosphine containing two phosphorus atoms, for example compounds of the formula (3) and/or (4), is employed, use is in most cases made of an aqueous phase which contains from 20 to 500 ppm, in particular from 30 to 150 ppm, preferably from 40 to 100 ppm, of rhodium.

The type of oleifinic compound to be reacted can to a certain extent also influence the amount of the compound of the formula (1) $R(OCH_2CH_2)_nOR^1$ to be used.

If the olefinic compound used is propene, it has frequently been found to be appropriate to carry out the reaction in the presence of an aqueous phase containing from 1 to 15% by weight, in particular from 3 to 10% by weight, of the compound of the formula (1).

If the olefinic compound used is butene, it has frequently been found to be appropriate to carry out the reaction in the presence of an aqueous phase containing from 5 to 25% by weight, in particular from 8 to 20% by weight, of the compound of the formula (1).

If the olefinic compound used is pentene, it has frequently been found to be appropriate to carry out the reaction in the presence of an aqueous phase containing from 5 to 35% by weight, in particular from 8 to 30% by weight, of the compound of the formula (1).

At this point, it may be mentioned for the sake of completeness that the compounds of the formula (1) $R(OCH_2CH_2)_nOR^1$, where R is hydrogen, a straight-chain or branched alkyl radical having from 1 to 4 carbon atoms or a hydroxyalkyl radical having from 1 to 4 carbon atoms, in particular hydrogen, an alkyl radical having from 1 to 2 carbon atoms or a hydroxyalkyl radical having from 1 to 3 carbon atoms, preferably hydrogen, methyl, hydroxymethyl or hydroxypropyl, and $R^1$ is hydrogen or a methyl radical, in particular hydrogen, are substances which dissolve in water to a sufficient extent.

Attention may be drawn at this point to the following compounds of the formula (1) in which $R^1$ is hydrogen and which are of particular interest.

Without making any claim as to completeness, compounds of the formula $R(OCH_2CH_2)_nOH$ which may be mentioned are polyethylene glycol of the formula $H(OCH_2CH_2)_nOH$ having a mean molecular weight of about 200 (PEG 200), 400 (PEG 400), 600 (PEG 600) or 1000 (PEG 1000), compounds of the formula $CH_3(OCH_2CH_2)_nOH$ having a mean molecular weight of about 350 (M 350), 500 (M 500) or 750 (M 750) or compounds of the formula $CH_3CHOHCH_2(OCH_2CH_2)_nOH$ having a mean molecular weight of about 300 (300 PR), 450 (450 PR), 600 (600 PR) or 1000 (1000 PR), in particular polyethylene glycol having a mean molecular weight of about 400 (PEG 400) and 600 (PEG 600), a compound of the formula $CH_3(OCH_2CH_2)_nOH$ having a mean molecular weight of 500 (M 500) or a compound of the formula $CH_3CHOHCH_2(OCH_2CH_2)_nOH$ having a mean molecular weight of 450 (450 PR) and 600 (600 PR).

For the purposes of the present invention, PEG 200 is a mixture of polyethylene glycols of the formula $H(OCH_2CH_2)_nOH$, where n is an integer from 3 to 6, PEG 400 is a mixture of polyethylene glycols of the formula $H(OCH_2CH_2)_nOH$, where n is an integer from 7 to 10, PEG 600 is a mixture of polyethylene glycols of the formula $H(OCH_2CH_2)_nOH$, where n is an integer from 11 to 16, and PEG 1000 is a mixture of polyethylene glycols of the formula $H(OCH_2CH_2)_nOH$, where n is an integer from 15 to 30. These mixtures can in each case be assigned a corresponding mean molecular weight of about 200 (PEG 200), about 400 (PEG 400), about 600 (PEG 600) or about 1000 (PEG 1000).

For the purposes of the present invention, M 350 is a mixture of compounds of the formula $CH_3(OCH_2CH_2)_nOH$, where n is an integer from 5 to 9, M 500 is a mixture of compounds of the formula $CH_3(OCH_2CH_2)_nOH$, where n is an integer from 9 to 13, and M 750 is a mixture of compounds of the formula $CH_3(OCH_2CH_2)_nOH$, where n is an integer from 12 to 20. These mixtures can in each case be assigned a corresponding mean molecular weight of about 350 (M 350), about 500 (M 500) or about 750 (M 750).

For the purposes of the present invention, 300 PR is a mixture of compounds of the formula $R(OCH_2CH_2)_nOH$, where R is a β-hydroxypropyl radical $CH_3CHOHCH_2-$ and n is an integer from 6 to 9, 450 PR is a mixture of compounds of the formula $R(OCH_2CH_2)_nOH$, where R is a β-hydroxypropyl radical $CH_3CHOHCH_2-$ and n is an integer from 8 to 14, 600 PR is a mixture of compounds of the formula $R(OCH_2CH_2)_nOH$, where R is a β-hydroxypropyl radical $CH_3CHOHCH_2-$ and n is an integer from 12 to 20, and 1000 PR is a mixture of compounds of the formula $R(OCH_2CH_2)_nOH$, where R is a β-hydroxypropyl radical $CH_3CHOHCH_2-$ and n is an integer from 18 to 26. These mixtures can in each case be assigned a corresponding mean molecular weight of about 300 (300 PR), about 450 (450 PR), about 600 (600 PR) or about 1000 (1000 PR).

In a number of cases it has been found to be useful to use a polyethylene glycol of the formula $H(OCH_2CH_2)_nOH$, where n is an integer from 3 to 50, in particular from 4 to 30, preferably from 5 to 20, particularly preferably from 6 to 12, as the compound of the formula (1).

It has also been found useful to use a compound (monoether) of the formula $R(OCH_2CH_2)_nOH$, where R is a methyl radical or a β-hydroxypropyl radical and n is an integer from 3 to 50, in particular from 4 to 30, preferably from 5 to 20, as the compound of the formula (1).

It is also possible to use any mixtures of the compounds of the formula (1), namely polyethylene glycols, polyethylene glycol ethers (monoethers) and polyethylene glycol diethers.

The reaction is carried out in the presence of hydrogen and carbon monoxide. The molar ratio of hydrogen to carbon monoxide can be selected within wide limits and is usually from 1:10 to 10:1, in particular from 5:1 to 1:5, preferably from 2:1 to 1:2, particularly preferably from 1.2:1 to 1:1.2. The process is particularly simple if hydrogen and carbon monoxide are used in a molar ratio of 1:1 or approximately 1:1.

In many cases, it is sufficient to carry out the reaction at a temperature of from 50 to 150° C., in particular from 100 to 140° C.

In many cases, it has been found to be useful to carry out the reaction at a pressure of from 10 to 200 bar, in particular from 20 to 150 bar, preferably from 30 to 80 bar.

During the reaction, good mixing of organic phase, aqueous phase and carbon monoxide/hydrogen must be ensured. This can be effected, for example, by intensive stirring and/or pumped circulation of organic and aqueous phases. The organic phase usually comprises the olefinic compound, the aldehydes produced and also small amounts of the aqueous phase, while the aqueous phase usually comprises rhodium, the sulfonated triarylphosphines, the compound of the formula (1), water and small amounts of the organic phase.

At this point, attention may again be drawn to the fact that the reaction conditions, in particular rhodium concentration, pressure and temperature, also depend on the type of olefinic compound to be hydroformylated. Comparatively reactive olefinic compounds require low rhodium concentrations, low pressures and low temperatures. In contrast, the reaction of relatively less reactive olefinic compounds requires higher rhodium concentrations, higher pressures and higher temperatures.

The process can be carried out particularly successfully if an α-olefinic compound is used. However, other olefinic compounds containing internal carbon-carbon double bonds can also be reacted with good results.

After the reaction is complete, the hydroformylation mixture is freed of carbon monoxide and hydrogen by depressurization and the reaction product, if appropriate after cooling, is separated from the aqueous phase comprising the catalyst and the compound of the formula (1) by phase separation.

The aqueous phase comprising the catalyst and the compound of the formula (1) can be returned to the process of the invention, while the organic phase containing the reaction product is worked up, for example by fractional distillation.

The process can be carried out continuously or batchwise.

The following examples illustrate the invention without restricting it.

EXPERIMENTAL PART

1. Hydroformylation of 1-pentene

EXAMPLE 1a)

Comparative Experiment to Examples 1b) to 1d) without Addition of Polyethylene Glycol)

I Preparation of the Catalyst Phase and Preformation 60 mg (0.233 mmol) of rhodium(III) acetate are dissolved in 39 ml of a 0.6 M aqueous solution of trisodium tri(m-sulfophenyl)phosphine (Na-TPPTS), corresponding to a molar ratio of rhodium to ligand of 1:100, and 21 ml of degassed distilled water and introduced under a stream of nitrogen into a 200 ml steel autoclave. This catalyst solution is heated at 125° C. under 25 bar of synthesis gas pressure ($CO/H_2=1/1$) for 3 hours while stirring, with the solution acquiring a yellow color.

II Hydroformylation 26.3 ml (240 mmol) of 1-pentene are added to the preformed catalyst solution from I at a reaction pressure of 30 bar and at 125° C. via an upstream 200 ml steel autoclave using slight overpressure. The ratio of olefin to rhodium is 1039:1. The hydroformylation reaction is started by switching on the magnetic stirrer. During a reaction time of 3 hours, the temperature is held at 125° C. and the reaction pressure is kept constant within a pressure band of ±2 bar by manual addition of synthesis gas. After 3 hours have elapsed, stirring and heating are switched off, the autoclave is cooled to from 40 to 50° C. and the upper product phase is separated from the catalyst phase in a separating funnel. Product phase and catalyst phase are weighed. The composition of the product phase is determined by means of gas chromatography and $^1$H-NMR spectroscopy, and the yield of hydroformylation products and the ratio of n-hexanal to iso-hexanal (2-methylpentanal) are determined from the composition. The rhodium content of the organic phase is, after digestion of the sample, determined by elemental analysis using graphite-furnace atomic absorption spectrometry. The yield of hydroformylation products is 49.4% and the n/iso ratio is 96:4. The organic phase contains 0.05 ppm of Rh. (Example 1a) in Table 1).

EXAMPLE 1b)

I Preparation of the Catalyst Phase and Preformation 60 mg (0.233 mmol) of rhodium(III) acetate are dissolved in 39 ml of a 0.6 M aqueous solution of trisodium tri(m-sulfophenyl)phosphine (Na-TPPTS). 5 ml of degassed polyethylene glycol 400 are added to this solution and the solution is made up to the total volume of 60 ml. This catalyst phase is introduced under a stream of nitrogen into a 200 ml steel autoclave and is heated at 125° C. under 25 bar synthesis gas pressure ($CO/H_2=1/1$) for 3 hours while stirring.

II Hydroformylation

Using a method similar to Example 1a), 30 ml (240 mmol) of 1-hexene are added to the preformed catalyst solution from I. The hydroformylation is carried out using a method similar to Example 1a) at 125° C. and 30 bar of synthesis gas. The product phase is analyzed using a method similar to Example 1a). The yield of hydroformylation product is 70.1% and the n/iso ratio is 96:4.(Example 1b) in Table 1)

EXAMPLE 1c)

The procedure of Example 1b) is repeated, except that 7 ml of degassed polyethylene glycol 400 in place of 5 ml of degassed polyethylene glycol 400 are now added to the catalyst phase and the total volume of the catalyst phase is made up to 60 ml. The preformation and hydroformylation conditions are identical to Example 1b). The yield of hydroformylation product is 81.1% and the n/iso ratio is 96:4. The organic phase contains 0.16 ppm of Rh. (Example 1c) in Table 1)

EXAMPLE 1d)

The procedure of Example 1b) is repeated, except that 10 ml of degassed polyethylene glycol 400 are added to the catalyst phase and the total volume of the catalyst phase is made up to 60 ml. The preformation and hydroformylation conditions are identical to Example 1b), except that the duration of the hydroformylation reaction is 210 min (3.5 hours). The yield of hydroformylation product is 88.0% and the n/iso ratio is 95:5. The organic phase contains 0.08 ppm of Rh. (Example 1d) in Table 1)

EXAMPLE 1e)

The procedure of Example 1b) is repeated, except that 21 ml of degassed polyethylene glycol 400 are added to the catalyst phase. The preformation and hydroformylation conditions are identical to Example 1b). The yield of hydroformylation product is 87.3% and the n/iso ratio is 91:9. The organic phase contains 0.85 ppm of Rh. (Example 1e) in Table 1)

EXAMPLE 1f)

Without Addition of a Compound of the Formula (1)

The procedure of Example 1a) is repeated, except that the hydroformylation reaction is carried out under 50 bar synthesis gas pressure. The yield of hydroformylation product is 74.8% and the n/iso ratio is 96:4. The organic phase contains 0.03 ppm of Rh. (Example 1f) in Table 1)

EXAMPLE 1g)

The procedure of Example 1f) is repeated, except that 5 ml of degassed polyethylene glycol 400 are added to the catalyst phase and the total volume of the catalyst phase is made up to 60 ml. The preformation and hydroformylation conditions are identical to Example 1f). The yield of hydroformylation product is 84.9% and the n/iso ratio is 95:5. (Example 1g) in Table 1)

EXAMPLE 1h) (as EXAMPLE 1g)

With a Longer Reaction Time

The procedure of Example 1g) is repeated, except that the hydroformylation reaction is carried out for 240 min (4 hours). The yield of hydroformylation product is 88.4% and the n/iso ratio is 96:4. The organic phase contains 0.09 ppm of Rh (Example 1h) in Table 1)

EXAMPLE 1i)

The procedure of Example 1f) is repeated, except that 7 ml of degassed polyethylene glycol 400 are added to the catalyst phase and the total volume of the catalyst phase is made up to 60 ml. The preformation and hydroformylation conditions are identical to Example 1f). The yield of hydroformylation product is 84.8% and the n/iso ratio is 95:5. (Example 1i) in Table 1)

EXAMPLE 1j)

The procedure of Example 1f) is repeated, except that 10 ml of degassed polyethylene glycol 400 are added to the catalyst phase and the total volume of the catalyst phase is made up to 60 ml. The preformation and hydroformylation conditions are identical to Example 1f). The yield of hydroformylation product is 87.5% and the n/iso ratio is 94:6. The organic phase contains 0.28 ppm of Rh (Example 1j) in Table 1)

EXAMPLE 1k)

Use of a Compound of the Formula $CH_3(OCH_2CH_2)_nOH$

The procedure of Example 1g) is repeated, except that, in place of 5 ml of polyethylene glycol 400, the same volume (5 ml) of a compound of the formula $CH_3(OCH_2CH_2)_nOH$, n=5 to 9 (commercial product of Hoechst, designation M 350) is added to the catalyst phase and the total volume of the catalyst phase is made up to 60 ml. The preformation and hydroformylation conditions are identical to Example 1g). The yield of hydroformylation product is 84.3% and the n/iso ratio is 95:5. The organic phase contains 0.07 ppm of Rh (Example 1k) in Table 1)

EXAMPLE 1l)

Use of a Compound of the Formula $CH_3CHOHCH_2(OCH_2CH_2)_nOH$ (n=8 to 14

The procedure of Example 1g) is repeated, except that, in place of 5 ml of polyethylene glycol 400 (PEG 400), the same volume (5 ml) of a compound of the formula $CH_3CHOHCH_2(OCH_2CH_2)_nOH$, n=8 to 14 (commercial product of Hoechst, designation 450PR) is added to the catalyst phase and the total volume of the catalyst phase is made up to 60 ml. The preformation and hydroformylation conditions are identical to Example 1g). The yield of hydroformylation product is 84.0% and the n/iso ratio is 95:5. The organic phase contains 0.09 ppm of Rh (Example 1l) in Table 1)

Examples 1g), 1k) and 1l) show that use of different compounds of the formula (1) gives comparable results in respect of yield of hydroformylation products, selectivity and rhodium content of the organic phase.

EXAMPLE 1m)

Use of a Compound of the Formula $H(OCH_2CH_2)_3OH$ (triethylene glycol)

The procedure of Example 1g) is repeated, except that, in place of 5 ml of polyethylene glycol 400 (PEG 400), the same volume of triethylene glycol is used and the total volume of the catalyst phase is made up to 60 ml. The preformation and hydroformylation conditions are identical to Example 1g). The yield of hydroformylation product is 79.8% and the n/iso ratio is 94:6. The organic phase contains 0.06 ppm of Rh (Example 1m) in Table 1)

EXAMPLE 1n)

Use of a Compound of the Formula $CH_3(OCH_2CH_2)_nOCH_3$ (n=3 to 6)

The procedure of Example 1g) is repeated, except that, in place of 5 ml of polyethylene glycol 400 (PEG 400), the same volume of a compound of the formula $CH_3(OCH_2CH_2)_nOCH_3$ (n=3 to 6, polyethylene glycol dimethyl ether) is used and the total volume of the catalyst phase is made up to 60 ml. The preformation and hydroformylation conditions are identical to Example 1g). The yield of hydroformylation product is 85.9% and the n/iso ratio is 95:5 (Example 1n) in Table 1)

Experiments using compounds of the formula (4) as triarylphosphine ligands containing two phosphorus atoms

EXAMPLE 1o)

Comparative Example to Examples 1p) and 1q) without Addition of a Compound of the Formula (I)

I Preparation of the Catalyst Phase and Preformation

The catalyst phase is made up from 7.5 mg (0.028 mmol) of rhodium(III) acetate, 1.8 ml of a 0.162 molar solution of sulfonated 2,2'-bis(diphenylphosphinomethyl)-1,1'-binaphthalene (Na-BINAS) corresponding to formula (4) and having a mean number of sulfonate groups of from 4 to 7, corresponding to a molar ratio of rhodium to ligand of 1:10, and 58 ml of degassed distilled water and introduced under a stream of nitrogen into a 200 ml steel autoclave. This catalyst solution is heated at 125° C. under 25 bar synthesis gas pressure ($CO/H_2=1/1$) for 3 hours while stirring.

II Hydroformylation

The hydroformylation reation is carried out under a synthesis gas pressure of 50 bar and the work-up and analysis of the organic phase is carried out using a method similar to experiment 1f). The yield of hydroformylation products is 76.1% and the n/iso ratio is 98:2 (Example 1o) in Table 1)

EXAMPLE 1p)

The procedure of Example 1o) is repeated, except that 5 ml of degassed polyethylene glycol 400 are added to the catalyst phase and the total volume of the catalyst phase is made up to 60 ml. The yield of hydroformylation product is 76.1% and the n/iso ratio is 98:2 (Example 1p) in Table 1)

EXAMPLE 1q)

The procedure of Example 1o) is repeated, except that 10 ml of a compound of the formula $CH_3(OCH_2CH_2)_nOH$, n=9 to 13 (commercial product of Hoechst, designation M 500) are added to the catalyst phase and the total volume of the catalyst phase is made up to 60 ml. The yield of hydroformylation product is 75.7% and the n/iso ratio is 98:2 (Example 1q) in Table 1)

2. Hydroformylation of 1-butene

EXAMPLE 2a)

Comparative Experiment to Examples 2b) to 2g) without Addition of an Additive of the Formula (1)

I Preparation of the Catalyst Phase and Preformation 60 mg (0.233 mmol) of rhodium(III) acetate are dissolved in 39 ml of a 0.6 M aqueous solution of trisodium tri(m-sulfophenyl)phosphine (Na-TPPTS), corresponding to a molar ratio of rhodium to ligand of 1:100, and 21 ml of degassed distilled water and introduced under a stream of nitrogen into a 200 ml steel autoclave. The catalyst solution thus prepared is heated at 125° C. under 25 bar synthesis gas pressure ($CO/H_2=1/1$) for 3 hours while stirring, with the solution acquiring a yellow color.

II Hydroformylation 12.46 g (224 mmol) of liquid 1-butene are added to the preformed catalyst solution from 1 at a reaction pressure of 30 bar and at 125° C. via an upstream 200 ml steel autoclave using slight overpressure. (The precise amount is determined by difference weighing.) The ratio of olefin to rhodium is 950:1. The hydroformylation reaction is started by switching on the magnetic stirrer. During a reaction time the temperature is held at 125° C. and the reaction pressure is kept constant within a pressure band of ±2 bar by manual addition of synthesis gas. The reaction is stopped after 120 minutes since no more synthesis gas is absorbed. The stirrer and the heating are switched off, the autoclave is cooled to from 40 to 50° C. and the upper product phase is separated from the catalyst phase in a separating funnel. The yield of hydroformylation products is determined by weighing and gas-chromatographic analysis of the organic phase; the ratio of n-pentanal to iso-pentanal (2-methylbutanal) is likewise determined by gas chromatography.

In this series of examples, the duration of the hydroformylation reaction is a measure of the hydroformylation rate. In this example, it is 120 minutes. The yield of hydroformylation products is 88.1% and the n/iso ratio is 96:4. The organic phase contains 0.07 ppm of Rh. (Example 2a) in Table 2)

EXAMPLE 2b)

I Preparation of the Catalyst Phase and Preformation 60 mg (0.233 mmol) of rhodium(III) acetate are dissolved in 39 ml of a 0.6 M aqueous solution of trisodium tri(m-sulfophenyl)phosphine (Na-TPPTS). 3 ml of degassed polyethylene glycol 400 are added to this solution and the solution is made up to a total volume of 60 ml. This catalyst phase is introduced under a stream of nitrogen into a 200 ml steel autoclave and preformed at 125° C. under 25 bar synthesis gas pressure ($CO/H_2=1/1$) for 3 hours while stirring.

II Hydroformylation 15.56 g (277 mmol) of 1-butene are added to the preformed catalyst solution from I, corresponding to a ratio of olefin to rhodium of 1186:1. The hydroformylation is carried out using a method similar to Example 2a) at 125° C. under 30 bar of synthesis gas. No further decrease in pressure occurs after 2 hours. The yield of hydroformylation product is 87.2% and the n/iso ratio is 96:4. The organic phase contains 0.07 ppm of Rh. Thus, with the amount of 1-butene increased by 23.6%, 22% more 1-butene is converted into hydroformylation products in the same reaction time without the n/iso selectivity being changed or the rhodium content of the organic phase rising. (Example 2b) in Table 2)

EXAMPLE 2c)

The catalyst phase is prepared and preformed using a method similar to Example 2a), except that 6 ml of degassed water are replaced by 6 ml of degassed polyethylene glycol. After the preformation, 13.34 g (238 mmol) of 1-butene are added, corresponding to a ratio of olefin to rhodium of 1017:1. The reaction is complete after only 90 minutes. The yield of hydroformylation product is 85.9% and the n/iso ratio is 96:4. Thus, taking into account the increased amount of 1-butene and the decreased reaction time compared to Example 2a), 38% more 1-butene are converted into hydroformylation products per unit time than in Example 2a). (Example 2c) in Table 1)

Example 2d)

The catalyst phase is prepared and preformed using a method similar to Example 2a), except that 9 ml of degassed water are replaced by 9 ml of degassed polyethylene glycol. After the preformation, 13.89 g (247 mmol) of 1-butene are added, corresponding to a ratio of olefin to rhodium of 1058:1. The hydroformylation reaction is complete after only 60 minutes. The yield of hydroformylation product is 89.3% and the n/iso ratio is 94:6. Thus, taking into account the increased amount of 1-butene and the decreased reaction time compared to Example 2a), 2.2 times as much 1-butene is converted into hydroformylation products per unit time than in Example 2a). The rhodium content of the organic phase is 0.2 ppm (Example 2d) in Table 2)

EXAMPLE 2e)

The catalyst phase is prepared and preformed using a method similar to Example 2a), except that 12 ml of degassed water are replaced by 12 ml of degassed polyethylene glycol 400. After the preformation, 13.57 g (242 mmol) of 1-butene are added, corresponding to a ratio of olefin to rhodium of 1034:1. The hydroformylation reaction is complete after only 45 minutes. The yield of hydroformylation product is 88.3% and the n/iso ratio is 94:6. Thus, taking into account the increased amount of 1-butene and the reduced reaction time compared Example 2a), 2.9 times as much 1-butene is converted into hydroformylation products per unit time than in Example 2a). (Example 2e) in Table 2)

EXAMPLE 2f)

Use of a Compound of the Formula $CH_3(OCH_2CH_2)_nOH$, n=9 to 13

The catalyst phase is prepared and preformed using a method similar to Example 2d), except that, in place of 9 ml of degassed polyethylene glycol 400, the same volume of a compound of the formula $CH_3(OCH_2CH_2)_nOH$, n =9 to 13 (commercial product of Hoechst, designation M 500) is used. After the preformation, 13.52 g (241 mmol) of 1-butene are added, corresponding to a ratio of olefin to rhodium of 1031:1. The hydroformylation reaction is complete after 60 minutes. The yield of hydroformylation product is 87.1% and the n/iso ratio is 95:5. Thus, taking into account the increased amount of 1-butene and the reduced reaction time compared to Example 2a), 2.13 times as much 1-butene is converted into hydroformylation products per unit time than in Example 2a). (Example 2f) in Table 2)

EXAMPLE 2g)

Use of a Compound of the Formula $CH_3(OCH_2CH_2)_nOCH_3$, n=3 to 6

The catalyst phase is prepared and preformed using a method similar to Example 2d), except that, in place of 9 ml of degassed polyethylene glycol 400, the same volume of a compound of the formula $CH_3(OCH_2CH_2)_nOCH_3$, n=3 to 6, is used. After the preformation, 12.41 g (221 mmol) of 1-butene are added, corresponding to a ratio of olefin to rhodium of 946:1. The hydroformylation reaction is complete after 50 minutes. The yield of hydroformylation product is 85.9% and the n/iso ratio is 95:5. Thus, taking into account the reduced reaction time, 40.0% more 1-butene is converted into hydroformylation products per unit time than in Example 2a). (Example 2g) in Table 2)

3. Hydroformylation of Propene 3.1 Description of the Experimental Apparatus The reaction apparatus used for the continuous hydroformylation of propene comprises a reactor (volume: 1l), a high-pressure separator connected downstream of the reactor and a phase separation vessel connected downstream of the high-pressure separator. During the hydroformylation, the reactor contains aqueous catalyst solution, unreacted propene, reaction products and synthesis gas. A stirrer installed in the reactor ensures good mixing.

Propene and water are metered in through an immersed tube projecting into the reactor. The addition of water serves to replace the amounts of water which are carried off with the hydroformylation product and removed from the aqueous catalyst solution. The reaction mixture is removed from the reactor through an immersed tube dipping into the reactor and is fed to a high-pressure separator. In the high-pressure separator, the reaction mixture is separated into gaseous and liquid constituents. The gaseous constituents containing essentially unreacted synthesis gas, small amounts of propene and reaction products are discharged from the high-pressure separator and, after cooling, separated from the organic products in a further, downstream separator. The unreacted synthesis gas freed of the organic materials is, after recompression, returned to the reaction. The liquid constituents containing essentially the aqueous catalyst solution and the reaction mixture are taken from the high-pressure separator and fed to the phase separation vessel connected downstream of the high-pressure separator. In the phase separation vessel, separation of reaction product and aqueous catalyst solution occurs. The reaction product which forms the upper phase is separated off and subsequently distilled. The lower phase comprising the aqueous catalyst solution is taken from the phase separation vessel and returned to the reactor by means of a pump. In this way, the aqueous catalyst solution is circulated.

3.2. Experimental Procedure

EXAMPLE 3.2.a)

Comparative Experiment without Addition of polyethylene glycol 400

The aqueous catalyst solution comprises 200 ppm of rhodium, trisodium tri(m-sulfophenyl)phosphine (Na-TPPTS) and rhodium in a molar ratio of 100:1. It is prepared by dissolving the corresponding amount of rhodium(III) acetate in an aqueous Na-TPPTS solution and preforming the catalyst solution at 122° C. under the conditions of the hydroformylation in the presence of synthesis gas ($CO/H_2$= 1/1). The reactor (volume: 1) equipped with a stirrer is 65% full of catalyst solution (650 ml) in the operating state. The total volume of catalyst solution is 850 ml, i.e. 200 ml of catalyst solution are present in the circulation system (high-pressure separator, phase separation vessel and lines) connected downstream of the reactor 83.5 g/h of propene and 0.0955 standard cubic meters per hour of synthesis gas are fed continuously to the reactor. The pressure is 50 bar and the reaction temperature is 122° C. The contents of the reactor are mixed vigorously by means of the stirrer. The mean residence time of the catalyst solution is 0.43 $h^{-1}$. The catalyst solution separated off in the phase separation vessel (1.5 l/h) is returned to the reactor. The propene conversion is 90%. This corresponds to a productivity of 0.2 kg of crude hydroformylation product per l of catalyst solution and hour (0.2 kg/(l of cat.×h)). The ratio of n-butyraldehyde to 2-methylpropanal is 93:7.

EXAMPLE 3.2.b)

Hydroformylation of Propene with Addition of polyethylene glycol 400

The procedure of Comparative Experiment 3.2.a) is repeated, except that the aqueous catalyst solution contains 9.5% by weight of polyethylene glycol having a mean molecular weight of 400 (PEG 400), the propene feed is increased to 100 g/h and the amount of synthesis gas is increased to 0.102 standard cubic meters per hour.

The propene conversion is now from 95% to 96%. This corresponds to a productivity of 0.25 kg of crude hydroformylation product per l of catalyst solution and hour (0.25 kg/(l of cat.×h)). The ratio of n-butyraldehyde to 2-methylpropanal is 91:9.

TABLE 1

Hydroformylation of 1-pentene
Constant conditions: T = 125° C., 240 mmol of olefin, total volume of catalyst phase = 60 ml

| | | | Additive | | | Pressure | | | Yield | | Rh |
|---|---|---|---|---|---|---|---|---|---|---|---|
| Example | Olefin:Rh | Ligand | Type | Amount [ml] | % by weight[1] | P:Rh | [bar] | T [° C.] | t [min] | % | n/iso[2] | [ppm][3] |
| 1a) | 1039 | TPPTS | — | — | — | 100:1 | 30 | 125 | 180 | 49.4 | 96:4 | 0.05 |
| 1b) | 1039 | TPPTS | PEG[4] | 5 | 8.7 | 100:1 | 30 | 125 | 180 | 70.1 | 96:4 | n.d. |
| 1c) | 1039 | TPPTS | PEG | 7 | 12.2 | 100:1 | 30 | 125 | 180 | 81.1 | 96:4 | 0.16 |
| 1d) | 1039 | TPPTS | PEG | 10 | 17.2 | 100:1 | 30 | 125 | 210 | 88.0 | 95:5 | 0.08 |

TABLE 1-continued

Hydroformylation of 1-pentene
Constant conditions: T = 125° C., 240 mmol of olefin, total volume of catalyst phase = 60 ml

| Example | Olefin:Rh | Ligand | Additive Type | Amount [ml] | % by weight[1] | P:Rh | Pressure [bar] | T [° C.] | t [min] | Yield % | n/iso[2] | Rh [ppm][3] |
|---|---|---|---|---|---|---|---|---|---|---|---|---|
| 1e) | 1039 | TPPTS | PEG | 21 | 35.0 | 100:1 | 30 | 125 | 180 | 87.3 | 91:9 | 0.85 |
| 1f) | 1039 | TPPTS | PEG | — | — | 100:1 | 50 | 125 | 180 | 74.8 | 96:4 | <0.03 |
| 1g) | 1039 | TPPTS | PEG | 5 | 8.7 | 100:1 | 50 | 125 | 180 | 84.9 | 95:5 | n.d. |
| 1h) | 1039 | TPPTS | PEG | 5 | 8.7 | 100:1 | 50 | 125 | 240 | 88.4 | 96:4 | 0.09 |
| 1i) | 1039 | TPPTS | PEG | 7 | 12.2 | 100:1 | 50 | 125 | 180 | 84.8 | 95:5 | n.d. |
| 1j) | 1039 | TPPTS | PEG | 10 | 17.2 | 100:1 | 50 | 125 | 180 | 87.5 | 94:6 | 0.28 |
| 1k) | 1039 | TPPTS | M 350[5] | 5 | 8.7 | 100:1 | 50 | 125 | 180 | 84.3 | 95:5 | 0.07 |
| 1l) | 1039 | TPPTS | 450 PR[6] | 5 | 8.7 | 100:1 | 50 | 125 | 180 | 84.0 | 95:5 | 0.09 |
| 1m) | 1039 | TPPTS | TEG[7] | 5 | 8.7 | 100:1 | 50 | 125 | 180 | 79.8 | 94:6 | 0.06 |
| 1n) | 1039 | TPPTS | DMPEG[8] | 5 | 8.7 | 100:1 | 50 | 125 | 180 | 76.3 | 95:05:00 | n.d. |
| 1o) | 5000 | BINAS | PEG | — | — | 10:1 | 50 | 125 | 180 | 59.5 | 99:1 | n.d. |
| 1p) | 5000 | BINAS | PEG | 5 | | 10:1 | 50 | 125 | 180 | 76.1 | 98:2 | n.d. |
| 1q) | 5000 | BINAS | M 500[9] | 10 | | 10:1 | 50 | 125 | 180 | 75.7 | 98:2 | n.d. |

[1]% by weight of additive based on the catalyst phase
[2]Ratio of n-hexanal to 2-methylpentanal (iso-hexanal)
[3]Rhodium content of the organic phase
[4]PEG = PEG 400 = $H(OCH_2CH_2)_nOH$; n = 7 to 10
[6]450 PR = $CH_3CHOHCH_2(OCH_2CH_2)_n$, n = 8 to 14
[7]TEG = $H(OCH_2CH_2)_3OH$
[8]DMPEG = $CH_3(OCH_2CH_2)_nOCH_3$; n = 3 to 6
[9]M 500 = $CH_3(OCH_2CH_2)_nOH$; n = 9 to 13

TABLE 2

Hydroformylation of 1-butene
Constant conditions: pressure = 50 bar, T = 125° C.,
use of TPPTS as ligand in a TPPTS:Rh ratio of 100:1, total volume of catalyst phase = 60 ml

| Example | 1-butene [mmol] | Olefin:Rh | Additive Type | Amount [ml] | % by weight[1] | t [min] | Yield % | n/iso[2] | Rh [ppm][3] | $R_r$ [mmol/min][4] |
|---|---|---|---|---|---|---|---|---|---|---|
| 2a) | 224 | 950:1 | — | — | — | 120 | 88.1 | 96:4 | 0.07 | 1644 |
| 2b) | 277 | 1186:1 | PEG[5] | 3 | 5 | 120 | 87.2 | 96:4 | 0.07 | 2013 |
| 2c) | 238 | 1017:1 | PEG | 6 | 10 | 90 | 85.9 | 96:4 | 0.1 | 2272 |
| 2d) | 247 | 1058:1 | PEG | 9 | 16 | 60 | 89.3 | 94:6 | 0.2 | 3676 |
| 2e) | 242 | 1034:1 | PEG | 12 | 21 | 45 | 88.3 | 94:6 | 0.16 | 4746 |
| 2f) | 241 | 1030:1 | M 500[6] | 9 | 16 | 60 | 87.1 | 95:5 | n.d. | 3545 |
| 2g) | 221 | 946:1 | DMPEG[7] | 9 | 16 | 50 | 85.9 | 95:6 | n.d. | 2308 |

[1]% by weight of additive based on the catalyst phase
[2]Ratio of n-pentanalto 2-methylbutanal (iso-pentanal)
[3]Rhodium content of the organic phase
[4]Mean reaction rate defined as mmol of aldehyde formed per minute of reaction time.
[5]PEG = PEG 400 = $H(OCH_2CH_2)_nOH$; n = 7 to 10
[6]M 500 = $CH_3(OCH_2CH_2)_nOH$; n = 9 to 13
[7]DMPEG = $CH_3(OCH_2CH_2)_nOCH_3$; n = 3 to 6

What is claimed is:

1. A process for preparing aldehydes, which comprises reacting an olefinically unsaturated compound having 3 carbon atoms with hydrogen and carbon monoxide at from 20 to 170° C. and from 1 to 300 bar in the presence of an aqueous phase comprising rhodium and sulfonated triarylphosphines as catalyst and from 1 to 15% by weight of a compound of the formula (1) $R(OCH_2CH_2)_nOR^1$, where the triarylphosphines contain at least three —$(SO_3)M$ radicals in which M are identical or different and M is H, an alkali metal ion, an ammonium ion, a quaternary ammonium ion, a ½ alkaline earth metal ion or ½ zinc ion, and where, in the formula (1), R is hydrogen, a straight-chain or branched alkyl radical having from 1 to 4 carbon atoms or a hydroxyalkyl radical having from 1 to 4 carbon atoms, $R^1$ is hydrogen or a methyl radical and n is an integer from 3 to 50.

2. A process for preparing aldehydes, which comprises reacting an olefinically unsaturated compound having 4 carbon atoms with hydrogen and carbon monoxide at from 20 to 170° C. and from 1 to 300 bar in the presence of an aqueous phase comprising rhodium and sulfonated triarylphosphines as catalyst and from 8 to 20% by weight of a compound of the formula (1) $R(OCH_2CH_2)_nOR^1$, where the triarylphosphines contain at least three —$(SO_3)M$ radicals in which M are identical or different and M is H, an alkali metal ion, an ammonium ion, a quaternary ammonium ion, a ½ alkaline earth metal ion or ½ zinc ion, and where, in the formula (1), R is hydrogen, a straight-chain or branched alkyl radical having from 1 to 4 carbon atoms or a hydroxyalkyl radical having from 1 to 4 carbon atoms, $R^1$ is hydrogen or a methyl radical and n is an integer from 3 to 50.

3. A process for preparing aldehydes, which comprises reacting an olefinically unsaturated compound having 5 carbon atoms with hydrogen and carbon monoxide at from 20 to 170° C. and from 1 to 300 bar in the presence of an aqueous phase comprising rhodium and sulfonated triarylphosphines as catalyst and from 8 to 30% by weight of a compound of the formula (1) $R(OCH_2CH_2)_nOR^1$, where the triarylphosphines contain at least three $—(SO_3)M$ radicals in which M are identical or different and M is H, an alkali metal ion, an ammonium ion, a quaternary ammonium ion, a ½ alkaline earth metal ion or ½ zinc ion, and where, in the formula (1), R is hydrogen, a straight-chain or branched alkyl radical having from 1 to 4 carbon atoms or a hydroxyalkyl radical having from 1 to 4 carbon atoms, $R^1$ is hydrogen or a methyl radical and n is an integer from 3 to 50.

4. The process as claimed in claim 1, wherein the olefinically unsaturated compound used is an aliphatic olefin having from 3 to 5 carbon atoms.

5. The process as claimed in claim 1, wherein the olefinic compound used is an aliphatic α-olefin having from 3 to 5 carbon atoms.

6. The process as claimed in claim 1, wherein the sulfonated triarylphosphines used are compounds of the formula (2)

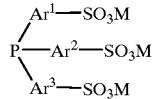

where $Ar^1$, $Ar^2$ and $Ar^3$ are identical or different and are each a phenyl or naphthyl radical and M are identical or different and are each an alkali metal ion, an ammonium ion, a quaternary ammonium ion or a ½ alkaline earth metal ion or ½ zinc ion.

7. The process as claimed in claim 1, wherein the sulfonated triarylphosphine used is a trisulfonated triphenylphosphine.

8. The process as claimed in claim 1, wherein the sulfonated triarylphosphine used is trisodium tri(m-sulfophenyl)phosphine.

9. The process as claimed in claim 1, wherein the aqueous phase is used in an amount corresponding to from $2 \times 10^{-6}$ to $5 \times 10^{-2}$ mol of rhodium per mol of olefinic compound.

10. The process as claimed in claim 6, wherein rhodium and sulfonated triarylphosphines of the formula (2) are used in a molar ratio of from 1:10 to 1:1000.

11. The process as claimed in claim 6, wherein rhodium and sulfonated triarylphosphines of the formula (2) are used in a molar ratio of from 1:50 to 1:200.

12. The process as claimed in claim 6, wherein the aqueous phase contains from 100 to 1000 ppm of rhodium when using sulfonated triarylphosphines of the formula (2).

13. The process as claimed in claim 6, wherein the aqueous phase contains from 200 to 500 ppm of rhodium when using sulfonated triarylphosphines of the formula (2).

14. The process as claimed in claim 6, wherein the aqueous phase contains from 300 to 400 ppm of rhodium when using sulfonated triarylphosphines of the formula (2).

15. The process as claimed in claim 1, wherein the sulfonated triarylphosphines used are compounds of the formula (3)

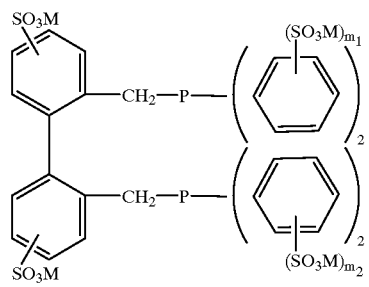

where $m_1$ and $m_2$ are, independently of one another, 0 or 1 and the compounds of the formula (3) contain from three to six $—SO_3M$ groups, where M is as defined above.

16. The process as claimed in claim 1, wherein the sulfonated triarylphosphines used are compounds of the formula (4)

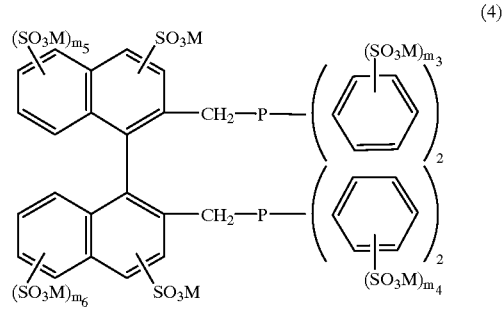

where $m_3$, $m_4$, $m_5$ and $m_6$ are, independently of one another, 0 or 1 and the compounds of the formula (4) have from four to eight $—SO_3M$ groups, where M is as defined above.

17. The process as claimed in claim 15, wherein rhodium and sulfonated triarylphosphines of the formula (3) are used in a molar ratio of 1:5 to 1:100.

18. The process as claimed in claim 15, wherein rhodium and sulfonated triarylphosphines of the formula (3) are used in a molar ratio of 1:5 to 1:50.

19. The process as claimed in claim 15, wherein rhodium and sulfonated triarylphosphines of the formula (3) are used in a molar ratio of 1:8 to 1:15.

20. The process as claimed in claim 15, wherein the aqueous phase contains from 20 to 500 ppm of rhodium when using sulfonated triarylphosphines of the formula (3).

21. The process as claimed in claim 15, wherein the aqueous phase contains from 30 to 150 ppm of rhodium when using sulfonated triarylphosphines of the formula (3).

22. The process as claimed in claim 15, wherein the aqueous phase contains from 40 to 100 ppm of rhodium when using sulfonated triarylphosphines of the formula (3).

23. The process as claimed in claim 1, wherein propene as olefinic compound is reacted in the presence of an aqueous phase containing from 3 to 10% by weight of the compound of the formula (1).

24. The process as claimed in claim 1, wherein the compound of the formula (1) used is a polyethylene glycol of the formula $H(OCH_2CH_2)_nOH$, where n is an integer from 3 to 50.

25. The process as claimed in claim 1, wherein the compound of the formula (1) used is a polyethylene glycol of the formula $H(OCH_2CH_2)_nOH$, where n is an integer from 4 to 30.

26. The process as claimed in claim 1, wherein the compound of the formula (1) used is a polyethylene glycol of the formula $H(OCH_2CH_2)_nOH$, where n is an integer from 6 to 12.

27. The process as claimed in claim 1, wherein the compound of the formula (1) used is a compound of the formula $R(OCH_2CH_2)_nOH$, where R is a methyl radical or β-hydroxypropyl radical and n is an integer from 3 to 50.

28. The process as claimed in claim 1, wherein the compound of the formula (1) used is a compound of the formula $R(OCH_2CH_2)_nOH$, where R is a methyl radical or β-hydroxypropyl radical and n is an integer from 4 to 30.

29. The process as claimed in claim 1, wherein the reaction is carried out at from 50 to 150° C.

30. The process as claimed in claim 1, wherein the reaction is carried out at from 100 to 140° C.

31. The process as claimed in claim 1, wherein the reaction is carried out at from 20 to 150 bar.

32. The process as claimed in claim 1, wherein the reaction is carried out at from 30 to 80 bar.

33. The process as claimed in claim 16 wherein rhodium and sulfonated triarylphosphines of the formula (4) are used in a molar ratio of 1:5 to 1:100.

34. The process as claimed in claim 16, wherein rhodium and sulfonated triarylphosphines of the formula (4) are used in a molar ratio of 1:5 to 1:50.

35. The process as claimed in claim 16, wherein rhodium and sulfonated triarylphosphines of the formula (4) are used in a molar ratio of 1:8 to 1:15.

36. The process as claimed in claim 16, wherein the aqueous phase contains from 20 to 500 ppm of rhodium when using sulfonated triarylphosphines of the formula (4).

37. The process as claimed in claim 16, wherein the aqueous phase contains 30 to 150 ppm of rhodium when using sulfonated triarylphosphines of the formula (4).

\* \* \* \* \*